(12) United States Patent
Fournier et al.

(10) Patent No.: US 10,973,984 B2
(45) Date of Patent: Apr. 13, 2021

(54) INJECTION DEVICE HAVING A NEEDLE PROTECTION SYSTEM

(71) Applicant: APTAR STELMI SAS, Villepinte (FR)

(72) Inventors: Arnaud Fournier, Paris (FR); Ghislain Fournier, La Rochelle (FR); Mickael Swal, Chauconin Neufmontiers (FR)

(73) Assignee: APTAR STELMI SAS, Villepinte (FR)

( * ) Notice: Subject to any disclaimer, the term of this patent is extended or adjusted under 35 U.S.C. 154(b) by 14 days.

(21) Appl. No.: 14/651,722

(22) PCT Filed: Dec. 11, 2013

(86) PCT No.: PCT/FR2013/053030
§ 371 (c)(1),
(2) Date: Jun. 12, 2015

(87) PCT Pub. No.: WO2014/091153
PCT Pub. Date: Jun. 19, 2014

(65) Prior Publication Data
US 2016/0106929 A1    Apr. 21, 2016

(30) Foreign Application Priority Data
Dec. 14, 2012   (FR) ..................................... 12 62066

(51) Int. Cl.
*A61M 5/32*   (2006.01)
*A61M 5/31*   (2006.01)
*A61M 5/20*   (2006.01)

(52) U.S. Cl.
CPC ........ *A61M 5/3202* (2013.01); *A61M 5/3204* (2013.01); *A61M 5/20* (2013.01); *A61M 2005/3109* (2013.01)

(58) Field of Classification Search
CPC .... A61M 5/3202; A61M 5/3204; A61M 5/20; A61M 2005/3109; A61M 5/3213
See application file for complete search history.

(56) References Cited

U.S. PATENT DOCUMENTS 4,742,910 A * 5/1988 Staebler .............. A61M 5/3213
                                                       206/365
4,986,818 A    1/1991 Imbert et al.
(Continued)

FOREIGN PATENT DOCUMENTS

DE   10 2008 003 185 A1   7/2009
EP    0 518 416 A1        12/1992
(Continued)

OTHER PUBLICATIONS

International Search Report for PCT/FR2013/053030 dated Mar. 21, 2014.
(Continued)

*Primary Examiner* — Lauren P Farrar
*Assistant Examiner* — Hamza A Darb
(74) *Attorney, Agent, or Firm* — Sughrue Mion, PLLC

(57) ABSTRACT

An injection device including a needle protection system, said injection device including a delivery needle (10) that is provided with a delivery orifice (11), said protection system comprising a removable needle guard (20) that, in a non-dispensing position, is adapted to be arranged on said needle (10) so as to protect and isolate said delivery orifice (11) of said needle (10), said needle guard (20) including an isolator portion (21) made of flexible material, said delivery orifice (11) of the needle (10) being poked into said isolator portion (21) in the non-dispensing position, said needle guard (10) including at least one outwardly-radial projection (25), said protection system further comprising an outer cap (30) that is provided with grip means (35, 35', 36; 38; 300) that are adapted to co-operate with said at least one radial projection (25) of said needle guard (20), such that moving said outer cap (30) in the longitudinal direction of said needle (10), away from said delivery orifice (11), removes said needle guard (20) from the non-dispensing position, said at least (Continued)

one radial projection (25) being arranged at the distal axial end of said needle guard (20), said at least one radial projection (25) being formed on a rigid outer structure (28) of said needle guard (20).

11 Claims, 4 Drawing Sheets

(56) References Cited

U.S. PATENT DOCUMENTS

| | | | | |
|---|---|---|---|---|
| 5,980,495 | A * | 11/1999 | Heinz | A61M 5/3202 128/919 |
| 6,585,702 | B1 | 7/2003 | Brunel | |
| 7,771,397 | B1 * | 8/2010 | Olson | A61M 5/3202 604/192 |
| 2002/0062108 | A1 * | 5/2002 | Courteix | A61M 5/3202 604/198 |
| 2010/0286619 | A1 * | 11/2010 | Abry | A61M 5/2033 604/192 |
| 2010/0286620 | A1 * | 11/2010 | Edginton | A61M 5/3202 604/192 |
| 2014/0243753 | A1 * | 8/2014 | Bostrom; Anders | A61M 5/3202 604/198 |

FOREIGN PATENT DOCUMENTS

| | | |
|---|---|---|
| EP | 1 208 861 A1 | 5/2002 |
| FR | 2 777 787 A1 | 4/1998 |
| GB | 2465389 A | 5/2010 |
| WO | 00/09186 A2 | 2/2000 |
| WO | 2004/110535 A | 12/2004 |
| WO | 2009/081103 A1 | 7/2009 |
| WO | 2009/087355 A1 | 7/2009 |
| WO | 2012/164397 A1 | 12/2012 |

OTHER PUBLICATIONS

International Preliminary Report on Patentability dated Jun. 18, 2015 from the International Searching Authority in counterpart application No. PCT/FR2013/053030.

* cited by examiner

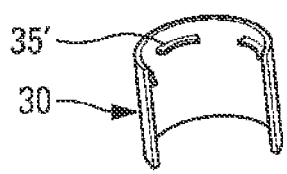
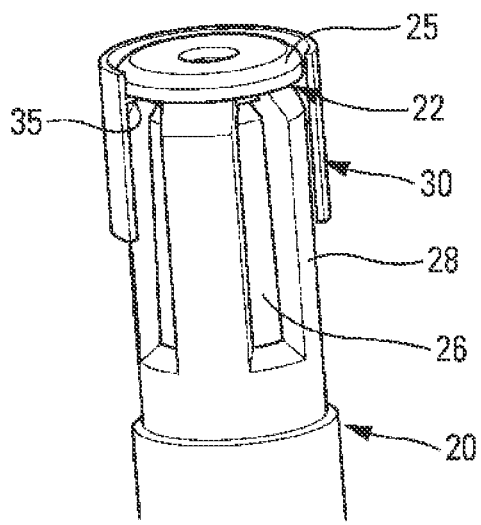
Fig. 8    Fig. 9
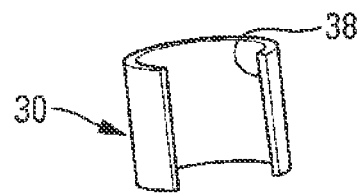
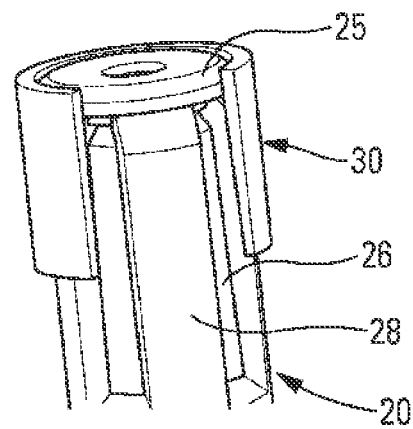
Fig. 10    Fig. 11
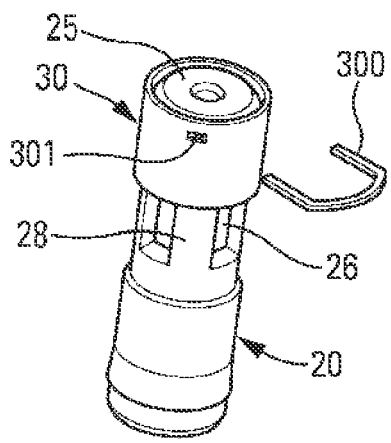
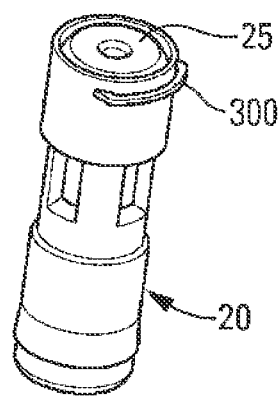
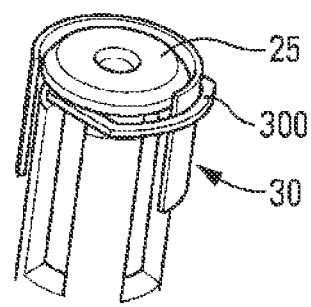
Fig. 12    Fig. 13    Fig. 14

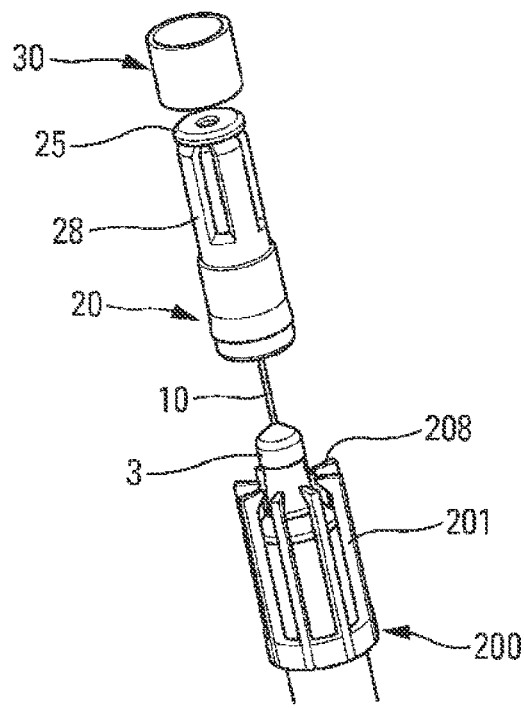 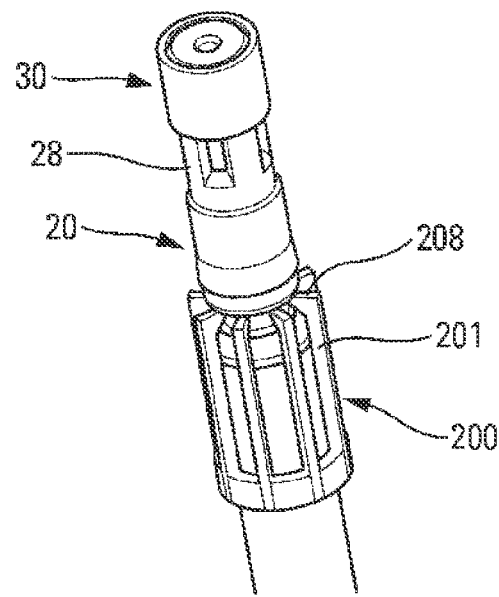
Fig. 15  Fig. 16
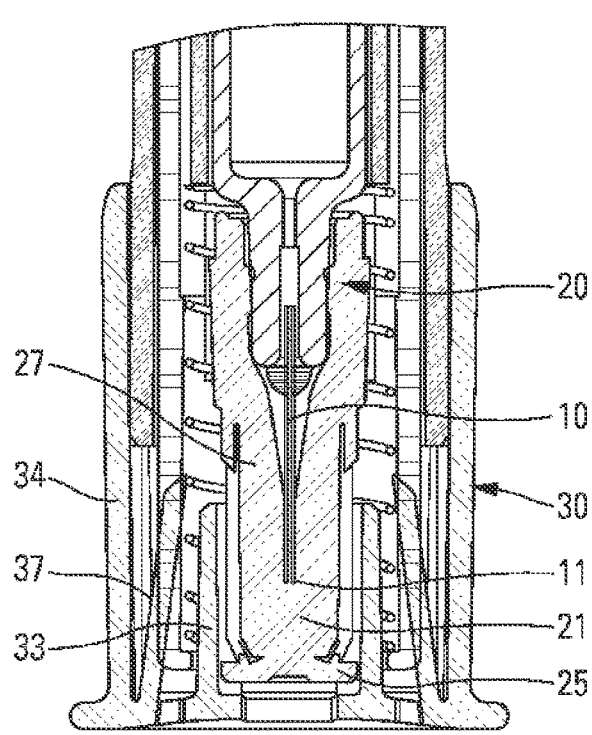 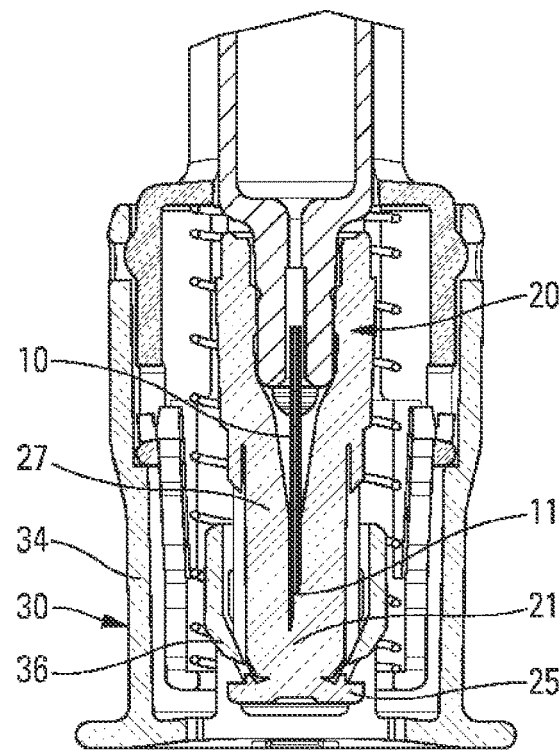
Fig. 17  Fig. 18

INJECTION DEVICE HAVING A NEEDLE PROTECTION SYSTEM

CROSS REFERENCE TO RELATED APPLICATIONS

This application is a National Stage of International Application No. PCT/FR2013/053030 filed Dec. 11, 2013, claiming priority based on French Patent Application No. 12 62066 filed Dec. 14, 2012, the contents of all of which are incorporated herein by reference in their entirety.

The present invention relates to an injection device including a needle protection system.

Injection devices are well known and generally comprise a body in which there is arranged a syringe containing a fluid to be delivered, said body incorporating delivery means that are adapted to move the piston of the syringe, thereby performing injection. One well known type of injection device is autoinjectors, in which injection is performed automatically by means of one or more springs. In that type of injection device, before being used, the needle of the syringe needs to be protected and in particular to be kept sterile.

To this end, it is known to use a removable needle guard, as described in documents FR 2 777 787 and FR 2 816 848, for example. That type of needle guard generally includes an isolator portion made of flexible material, into which the end of the needle incorporating the delivery orifice is poked in a protection or a non-protection position. When the user wishes to use the injection device, the user removes the needle guard manually so as to release the needle and thus make it possible to inject the fluid.

A problem that occurs with that type of device relates to the safety of people that operate the injection device, and in particular to the risk of being pricked by the needle when the needle guard has been removed or during the stage of removing said needle guard. In addition, in particular in the context of autoinjectors, removing the needle guard from its protection or non-dispensing position must also be reliable and as simple as possible.

Documents WO 2009/081103, WO 2012/164397, FR 2 777 787, EP 0 518 416, WO 00/09186, U.S. Pat. No. 4,986,818, WO 2004/110535, WO 2009/87355, and DE 10 2008 003185 describe prior-art devices.

An object of the present invention is to provide an injection device including a needle protection system that does not have the above-mentioned drawbacks.

In particular, an object of the present invention is to provide such a protection system that is simple and inexpensive to manufacture and to assemble, and that is reliable in use.

The present invention thus provides an injection device including a needle protection system, said injection device including a delivery needle that is provided with a delivery orifice, said protection system comprising a removable needle guard that, in a non-dispensing position, is adapted to be arranged around said needle so as to protect and isolate said delivery orifice of said needle, said needle guard including a hollow lateral body and an isolator portion, at least said isolator portion being made of flexible material, said delivery orifice of the needle being poked into said isolator portion in the non-dispensing position, said needle guard including at least one outwardly-radial projection, said protection system further comprising an outer cap that is provided with grip means that are adapted to co-operate with said at least one radial projection of said needle guard, such that moving said outer cap in the longitudinal direction of said needle, away from said delivery orifice, removes said needle guard from the non-dispensing position, said at least one radial projection being arranged at the outer axial end of said needle guard, said at least one radial projection being formed on a rigid outer structure of said needle guard.

Advantageously, said at least one radial projection is formed by a disk that defines a peripheral radial projection.

Advantageously, said grip means comprise at least one radial shoulder that extends radially towards the inside of said outer cap and that co-operates, in particular by snap-fastening, with said at least one radial projection of said needle guard.

Advantageously, said at least one radial shoulder is formed by a peripheral radial flange or by a plurality of radial-flange portions that are distributed over the periphery.

Advantageously, said at least one shoulder is formed by a deformable tab.

Advantageously, said grip means comprise a conical inside surface that co-operates, by jamming and/or friction, with the radially-outer edge of said at least one radial projection.

Advantageously, said grip means are formed integrally with said cap.

In a variant, said grip means are formed on an inner part that is movable relative to said cap.

Advantageously, a ring of said injection device co-operates with said needle guard in the non-dispensing position so as to form a mechanical abutment while putting the outer cap in place around said needle guard.

Advantageously, said injection device is an autoinjector.

These characteristics and advantages and others of the present invention appear more clearly from the following detailed description, given by way of non-limiting examples, and with reference to the accompanying drawings, and in which FIG. 1 is a diagrammatic and partially cut-away perspective view of an injection device incorporating a needle protection system in a first embodiment of the present invention, with the needle guard removed;

FIGS. 8 and 9 are views similar to the views in FIGS. 4 and 5, showing still another variant embodiment of the present invention;

FIGS. 10 and 11 are views similar to the views in FIGS. 4 and 5, showing still another variant embodiment of the present invention;

FIGS. 12 to 14 are diagrammatic views showing still another variant embodiment of the present invention;

FIGS. 15 and 16 are diagrammatic views showing still another variant embodiment of the present invention;

FIG. 17 is a diagrammatic section view of another embodiment that is not covered by the present invention, shown in its non-dispensing position; and FIG. 18 is a view similar to the view in FIG. 17, taken from another view point.

Figure 1:
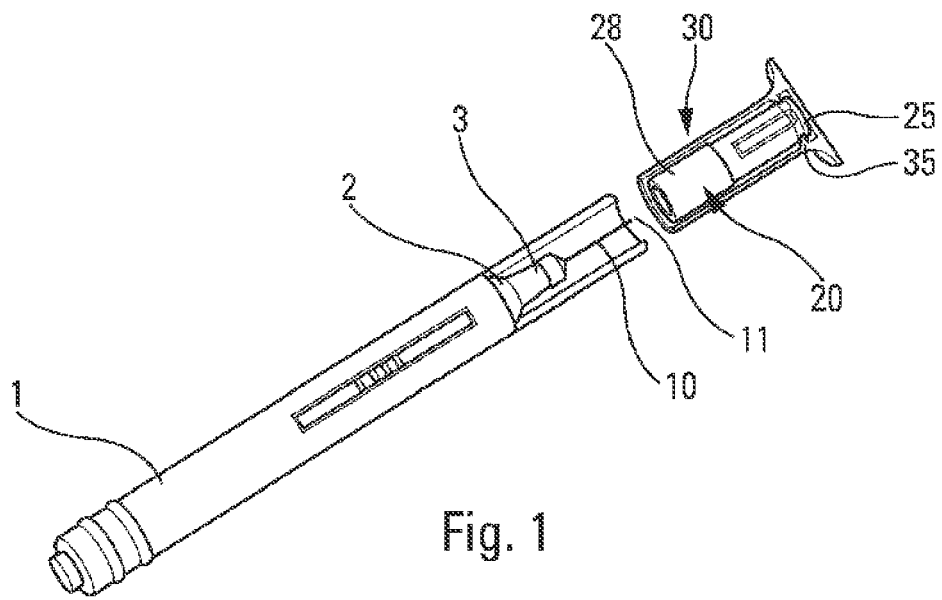
Figure 2:
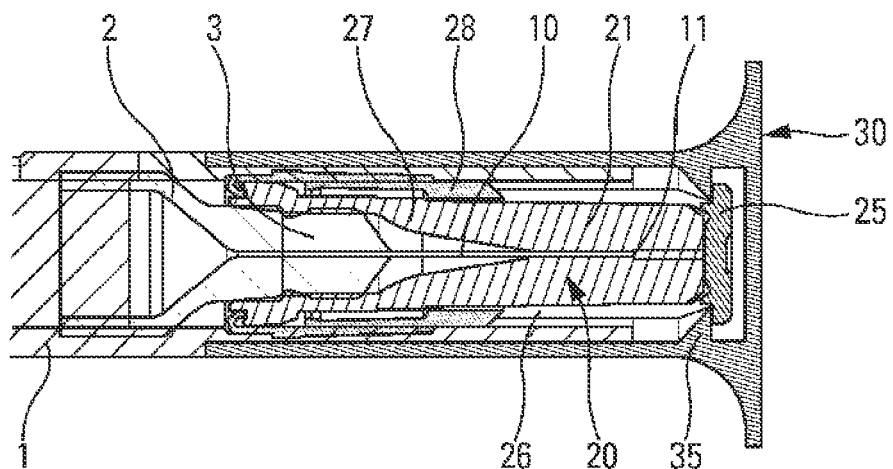
FIG. 2 is a diagrammatic section view of a portion of the device shown in FIG. 1.

FIGS. 1 to 2 show a first embodiment of the invention. This first embodiment shows, in very diagrammatic manner, an injection device such as an autoinjector. The autoinjector includes an outer body 1 that may contain a syringe 2 that forms a reservoir containing the fluid to be injected. Said syringe 2 is provided with a leading end 3 that is provided with a needle 10, said needle having a delivery orifice 11 at its distal axial end, i.e. its axial end the furthest from said reservoir.

A removable needle guard 20 is provided for covering said needle 10 in a non-dispensing position that is shown in FIG. 2. In known manner, the needle guard 20 may include an isolator portion 21 that is made of flexible material and into which the delivery orifice 11 of the needle 10 is poked in the non-dispensing position, thereby isolating said needle and thus keeping the contents of the syringe 2 sterile. In known manner, said needle guard 20 may include a hollow lateral body 27 that is open at a proximal axial end where it becomes engaged on the leading end 3 of the syringe 2, and that is closed at the distal other axial end by said isolator portion 21 that is made of flexible material. Optionally, the lateral body 27 may also be made of flexible material, as shown in the embodiments in the figures.

An outer structure 28 that is made of rigid material is provided around said lateral body 27, in particular so as to stiffen the needle guard 20. Dual-material needle guards of this type are well known and, in particular, are described in the above-mentioned documents. By way of example, the flexible portion of the needle guard may be made of rubber or of thermoplastic elastomer (TPE). The rigid portion may be made of any appropriate plastics material, e.g. polypropylene (PP). In a variant, the rigid portion could also be made partially or entirely of metal, e.g. of steel.

In the invention, the needle guard 20 includes at least one radial projection 25 that extends radially outwards. In particular, the projection 25 may be made in the form of a disk. The radial projection 25 is fastened or formed on the distal axial end of the needle guard 20, as shown in the figures. In a variant, it could have a plurality of projections that are distributed around the periphery of the distal axial end of said needle guard.

In the invention, and as shown in the embodiments in FIGS. 1 to 16, said radial projection 25 is formed on said rigid outer structure 28. As shown in the figures, the radial projection is arranged only at a distal axial end of the needle guard. Advantageously, the rigid outer structure 28 may include one or more lateral slots 26. Optionally, a radial recess 22 may be formed between said rigid outer structure 28 and the radial projection 25.

In a variant that is not covered by the invention, shown in FIGS. 17 and 18, the radial projection 25 is formed directly on said lateral body 27 of the needle guard. This configuration presents the drawback of requiring a complex needle guard to be made out of flexible material and that incorporates said radial projection. In addition, since the radial shoulder is made of flexible material, it becomes deformable, which might impede its operation. In this variant, the outside diameter of said radial projection 25 is preferably greater than the outside diameter of said lateral body 27, as can be seen in FIGS. 17 and 18. It should be observed that the embodiment in FIGS. 17 and 18 could apply to a needle guard with a rigid outer structure, in which event it would be covered by the invention.

The protection system of the invention also includes an outer cap 30 that becomes engaged around said needle guard 20, and that includes grip means that are adapted to co-operate with said at least one distal radial projection 25 of said needle guard 20.

Advantageously, the grip means may include at least one radial shoulder that extends radially inwards from an inside surface of said cap.

Thus, with reference to the embodiment in FIGS. 1 and 2, it can be seen that the radial shoulder is formed by a continuous peripheral flange 35 that projects radially inwards from the inside surface of the outer cap 30, and that becomes snap-fastened below said distal radial projection 25 of the needle guard.

When the user removes the cap 30 by moving it axially in the longitudinal direction of the needle 10 away from the delivery orifice 11, the needle guard 20 is removed from its protecting or non-dispensing position, thereby releasing the needle, as can be seen in FIG. 1.

FIGS. 4 to 9 show various variant embodiments of said at least one radial shoulder of the cap 30.

Thus, while in FIG. 2 the shoulder is formed by a peripheral radial flange 35 inside the cap 30, a plurality of radial-flange portions 35' could very well be provided, distributed over the periphery, as shown in FIG. 8.

Figure 4:
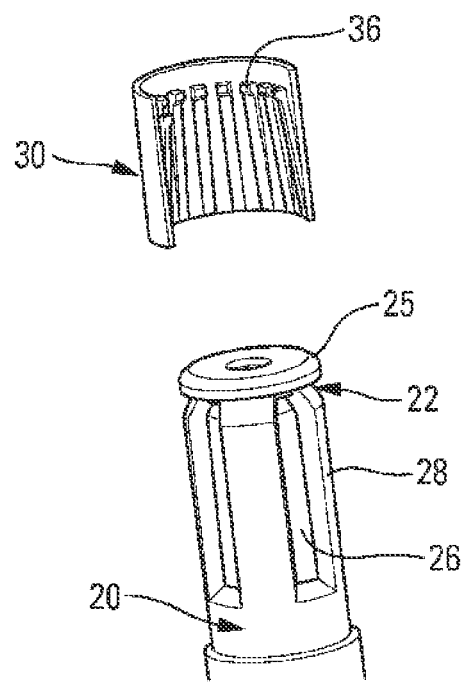
FIGS. 4 and 5 are diagrammatic and partially cut-away perspective views of a variant embodiment of the present invention, respectively in its non-assembled position and in its assembled position.
Figure 5:
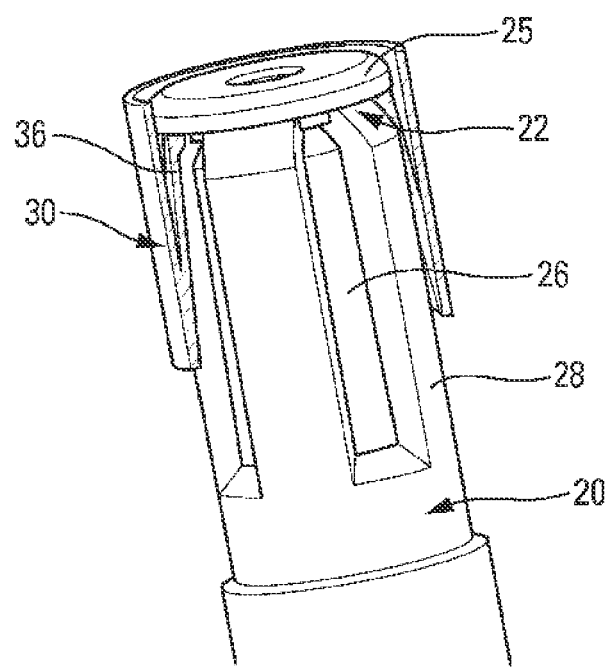
Figure 6:
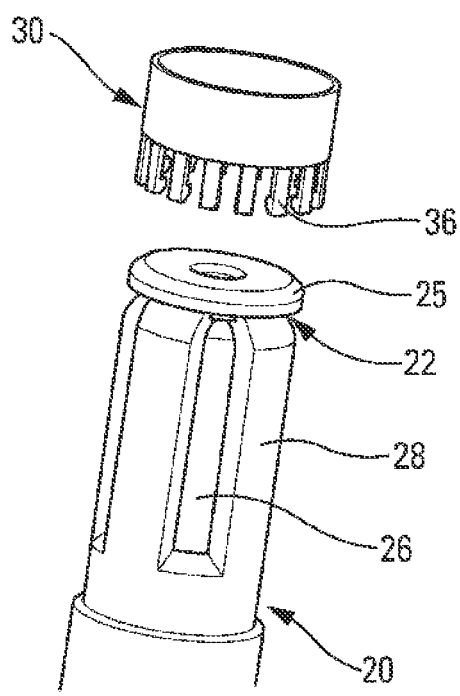
FIGS. 6 and 7 are views similar to the views in FIGS. 4 and 5, showing another variant embodiment of the present invention.
Figure 7:
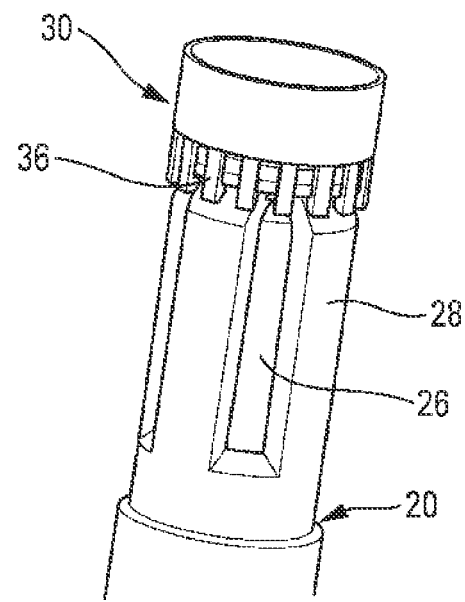

In a variant, it is also possible to provide deformable tabs 36 that may be either tabs that are oriented axially towards said radial projection 25, as can be seen in FIGS. 4 and 5, or conventional snap-fastener tabs that are oriented in the opposite direction, as shown in FIGS. 6 and 7.

Naturally, any type of shoulder that is adapted to co-operate with any type of projection may be envisaged in the context of the present invention, for enabling the outer cap 30 to co-operate with the needle guard 20.

FIGS. 10 and 11 show a variant embodiment in which the outer cap 30 does not include an inner radial shoulder, but a conical inner surface that co-operates, by jamming and/or friction, with the radially-outer edge of the distal radial projection 25.

FIGS. 12 to 14 show still another variant in which an outer grip member 300 co-operates with the outer cap 30 and with said at least one radial projection 25 of the needle guard 20. Advantageously, the outer grip member 300 is made in the form of a U-shaped clip or pin that, after putting the outer cap 30 in place on the needle guard 20, is inserted through openings 301 of the outer cap 30, below said radial projection 25, as can be seen in FIG. 14. This embodiment adds an additional part, but makes assembling the outer cap 30 less complex.

The use of a radial projection 25, formed at the outer axial end of the needle guard 20, that co-operates with grip means of the outer cap 30 is particularly simple to manufacture and to assemble, and particularly reliable in use.

FIGS. 15 and 16 show a variant embodiment in which a ring 200 is added around the syringe 2, in the proximity of the leading end 3 of said syringe. The purpose of the ring 200 is to co-operate with the rear axial edge of the rigid structure 28 of the needle guard 20. The ring 200 may be a component element of the injection device. It may include holding fingers 201 having front axial edges 208 that co-operate with the needle guard 20. While the outer cap 30 is being put in place on the needle guard 20, the fingers 201 make it possible, by mechanical abutment, to prevent said needle guard from moving in translation. Thus, the forces generated while putting the outer cap in place are transmitted directly via the contact between the rigid structure 28 of the needle guard 20 and the holding fingers 201 of the ring 200. In this way, the needle guard 20 does not move while the outer cap is being put in place, thereby making it possible to preserve the integrity of the device, and avoid the needle being damaged.

Figure 3:
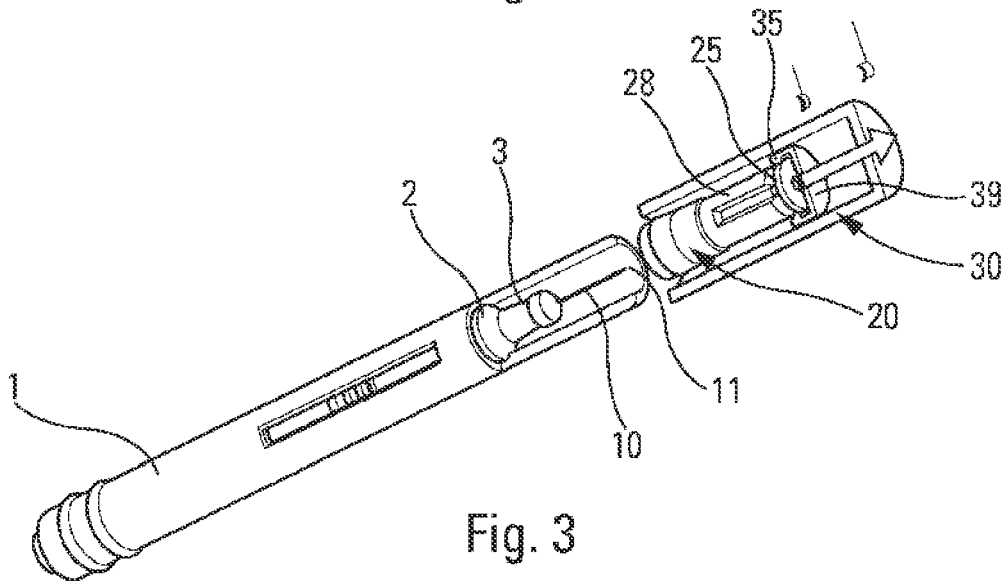
FIG. 3 is a view similar to the view in FIG. 1, showing a second embodiment of the present invention.

FIG. 3 shows a variant embodiment of the device in FIGS. 1 and 2, in which said radial shoulder 35 of the outer cap 30 is not formed integrally with the cap 30, as occurs in particular in the embodiment in FIGS. 1 and 2, but it is formed on a movable part 39 that is movable inside said outer cap 30.

FIGS. 17 and 18 show another embodiment that is not covered by the present invention, since the needle guard does not include a rigid outer structure. In this variant, the outer cap 30 has a shape that is more complex. Nevertheless, the cap 30 in FIGS. 17 and 18 could also apply to a needle guard with a rigid outer structure supporting the distal radial projection 25, in which event it would be covered by the present invention.

In this variant embodiment, the outer cap 30 comprises an inner sleeve 33 and an outer sleeve 34. The outer sleeve 34 forms the outer portion of the outer cap 30, while the inner sleeve 33 co-operates with said needle guard 20, in particular with said distal radial projection 25. Said inner sleeve 33 of the outer cap 30 may be made with deformable tabs 36 that project inwards, as can be seen in FIG. 18, and that are distributed around the periphery of said inner sleeve. In particular, the tabs 36 may be formed at longitudinal or axial openings that are provided in said inner sleeve 33.

Stabilizing tabs 37 for stabilizing the outer cap 30 relative to the autoinjector may be provided between the outer sleeve 34 and the inner sleeve 33, as can be seen in FIG. 17.

Other modifications may also be envisaged without going beyond the ambit of the present invention, as defined by the accompanying claims.

The invention claimed is:

1. An injection device including a needle protection system, said injection device including a delivery needle that is provided with a delivery orifice, said protection system comprising a removable needle guard that, in a non-dispensing position, is adapted to be arranged around said needle so as to protect and isolate said delivery orifice of said needle, said needle guard including a flexible portion comprising a hollow lateral body and an isolator portion made of flexible material and a rigid outer structure made of an integral one-piece construction fixed to and around said flexible portion, said delivery orifice of the needle being poked into said isolator portion in the non-dispensing position, wherein said needle guard includes at least one outwardly-radial projection, said protection system further comprising an outer cap that is provided with a grip that is adapted to co-operate with said at least one radial projection of said needle guard, such that moving said outer cap in a longitudinal direction of said needle, away from said delivery orifice, removes said needle guard from the non-dispensing position, said at least one radial projection being arranged only at a distal axial end of said needle guard, said at least one radial projection being formed on said rigid outer structure of said needle guard, wherein said grip comprises at least one radial shoulder that extends radially towards an inside of said outer cap and that co-operates by axially snap-fastening with said at least one radial projection of said needle guard to secure said outer cap to said needle guard; and wherein said flexible portion comprises a flexible distal end near the distal end of the needle guard and a flexible proximal end near a proximal end of the needle guard, and said rigid outer structure comprises a corresponding rigid distal end and a corresponding rigid proximal end, said flexible portion is fixed inside said rigid outer structure between said rigid distal end and said rigid proximal end, with said rigid proximal end cooperating with said flexible proximal end and said rigid distal end cooperating with said flexible distal end.

2. A device according to claim 1, wherein said at least one radial projection is formed by a disk that defines a peripheral radial projection.

3. A device according to claim 1, wherein said at least one radial shoulder is formed by a peripheral radial flange or by a plurality of radial-flange portions that are distributed over an inner peripheral surface of the outer cap.

4. A device according to claim 1, wherein said at least one shoulder is formed by a deformable tab.

5. A device according to claim 1, wherein said grip comprises a conical inside surface that co-operates, by jamming and/or friction, with a radially-outer edge of said at least one radial projection.

6. A device according to claim 1, wherein said grip is formed integrally with said cap.

7. A device according to claim 1, wherein said grip is formed on an inner part that is movable relative to said cap.

8. A device according to claim 1, wherein a ring of said injection device co-operates with said needle guard in the non-dispensing position so as to form a mechanical abutment while putting the outer cap in place around said needle guard.

9. A device according to claim 1, wherein said injection device is an autoinjector.

10. The device according to claim 1, wherein the at least one radial projection has a disc shape.

11. The device according to claim 1, wherein the at least one radial shoulder that extends radially towards the inside of the outer cap co-operates with an inclined surface of the at least one radial projection so as to achieve one-way axially snap-fastening with the at least one radial projection of said needle guard.

* * * * *